United States Patent
Shibuta et al.

[11] Patent Number: 5,152,897
[45] Date of Patent: Oct. 6, 1992

[54] METHOD FOR THE PURIFICATION OF A BIFIDOBACTERIA-PROLIFERATING SUBSTANCE

[75] Inventors: Takanobu Shibuta; Yasuyuki Yoshida, both of Tokyo, Japan

[73] Assignee: The Calpis Food Industry Co., Ltd., Tokyo, Japan

[21] Appl. No.: 753,310

[22] Filed: Aug. 30, 1991

[30] Foreign Application Priority Data

Sep. 4, 1990 [JP] Japan .................. 2-233839

[51] Int. Cl.$^5$ ........................................... B01D 61/16
[52] U.S. Cl. .................................. 210/639; 210/766; 210/774
[58] Field of Search ............... 210/702, 634, 639, 644, 210/649–654, 749, 766, 776; 435/104

[56] References Cited

U.S. PATENT DOCUMENTS

| | | |
|---|---|---|
| 4,054,679 | 10/1977 | Melcer et al. . |
| 4,071,406 | 1/1978 | Kanda .................. 435/104 |
| 4,482,574 | 11/1984 | Lee . |
| 4,902,673 | 2/1990 | Hayakawa et al. . |

FOREIGN PATENT DOCUMENTS

| | | |
|---|---|---|
| 0404425 | 12/1990 | European Pat. Off. . |
| 62-155082 | 7/1962 | Japan . |
| 51-142566 | 12/1976 | Japan . |
| 55-85390 | 6/1980 | Japan . |
| 58-32600 | 7/1983 | Japan . |
| 59-179064 | 10/1984 | Japan . |
| 60-66978 | 4/1985 | Japan . |
| 61-86907 | 5/1986 | Japan . |
| 63-0072012 | 10/1988 | Japan . |

*Primary Examiner*—Frank Sever
*Attorney, Agent, or Firm*—Nixon & Vanderhye

[57] ABSTRACT

A method for the purification of a bifidobacteria-proliferating substance is provided which comprises adjusting the temperature of soybean whey to 50° to 100° C. and the pH thereof to 6.5 to 10 either by adding an alkaline substance to the whey and heating it or by heating the whey and adding the alkaline substance, removing the formed precipitate, ultrafiltering the resulting liquid phase part to obtain as the permeate an aqueous solution of a bifidobacteria-proliferating substance, and if necessary subjecting the permeate to further purification steps, i.e. active carbon or adsorbing resin treatment, electrodialysis and ion exchange resin treatment. By the step of the alkali substance treatment and heating in this invention, permeate flux in the succeeding ultrafiltration step is remarkably enhanced. Further, a bifidobacteria-proliferating substance having a high quality can effectively be obtained by the present purification method.

6 Claims, 3 Drawing Sheets

METHOD FOR THE PURIFICATION OF A BIFIDOBACTERIA-PROLIFERATING SUBSTANCE

BACKGROUND OF THE INVENTION

This invention relates to a method for the purification of a substance capable of proliferating intestinal bacteria belonging to the genus Bifidobacterium, i.e. bifidobacteria, and more detailedly relates to a method for the purification of a bifidobacteria-proliferating substance in soybean whey.

Intestinal bifidobacteria are generally regarded as phsiologically preferred for infants to adults. Particularly, they are said to have effects of the prevention of infection in the intestinal tract, the reinforcement of immune function, the inhibition of putrefaction in the intestine, the decomposition of carcinogens, the production of vitamins, etc.

In order to exert such effects, it is important to make an environment in the intestine such that bifidobacteria take root and proliferate, and as a method therefor it has been tried to maintain the number of the bifidobacteria in the intestine to a high level by orally administering a substance promoting the proliferation of bifidobacteria solely or together with a Bifidobacterium culture.

Heretofore, oligosaccharides contained in soybeans, such as stachyose and raffinose, are known as saccharides proliferating bifidobacteria. However, the effect of bifidobacteria proliferation of these saccharides is inferior to that of the bifidobacteria-proliferating substance contained in soybean milk.

As for bifidobacteria-proliferating substances contained in soybean milk, it is disclosed, for example in Japanese Published Patent Application Nos. 142566/1976 and 85390/1980, etc. that soybean milk is effective for the growth of bifidobacteria. However, these publications do not disclose which ingredients are effective.

Further, processes for the preparation of a bifidobacteria proliferation-promoting substance from soybean milk (an extract of defatted soybean with water) are reported in Japanese Published Patent Application Nos. 179064/1984, 66978/1985 etc. and the processes comprise a protein removal step wherein phosphoric acid or hydrochloric acid is added to soybean milk, a neutralization step wherein calcium hydroxide is used in the presence of calcium chloride, a heating and precipitate separation step and a desalting and concentration step (reverse osmotic pressure treatment).

However, in the heating step (100° C., 10 minutes) in the preparation processes there is a problem that the amino acids and the reducing saccharides in the soybean whey react. Further, the liquid at the stage when the heating and precipitate separation step was completed contains various impurities, and when the liquid is directly subjected to reverse osmotic pressure treatment, the reverse osmosis membrane is apt to be fouled and clogged and permeate flux decreases. Further, the purification degree of the reverse osmotic pressure-treated liquid is insufficient (small amounts of colored substances, salts, proteins, etc. are contained) and the use thereof is limited.

On the other hand, the present inventors proposed a process for the production of a bifidobacteria-proliferating substance which comprises extracting defatted soybeans, as the raw material, with an aqueous alcohol solution and removing the alcohol. Further, the present inventors invented as a method including the improvement of this process a method for the purification of a bifidobacteria-proliferating substance which comprises ultrafiltering soybean whey, subjecting the permeate to active carbon treatment and electrodialyzing the liquid after the removal of the active carbon. This method was filed as U.S. patent application Ser. No. 07/537,664 (European Patent Application No. 90306429.3/1990). In this method an aqueous solution of a bifidobacteria-proliferating substance is obtained as an electrodialysis-treated liquid by carrying out the ultrafiltration using an ultrafiltration membrane having a fractional molecular weight of 20,000 to 100,000 to remove high molecular substances, mainly proteins having a molecular weight equal to or more than the fractional molecular weight, subjecting the permeate to active carbon treatment to remove low molecular proteins, particularly 2 S proteins (S:Svedbery unit; a unit of sedimentation coefficient) becoming a cause of membrane fouling in the succeeding electrodialysis, colored materials, etc., and electrodialyzing the liquid after the removal of the active carbon to remove salts contained in a small amount, and subjecting the electrodialyzed liquid to ion exchange resin treatment to obtain an aqueous solution of a bifidobacteria-proliferating substance. This ion exchange resin-treated liquid is substantially free of proteins and is usually colorless and transparent, and therefore a product of high completion degree such that it can be applied as a bifidobacteria-proliferating substance as such, or as syrup after concentration or as a powder after successive drying.

However depending on soybean whey to be used, there sometimes arises a case where when the concentration factor of the liquid to be treated is raised in the ultrafiltration step in the method of U.S. patent application Ser. No. 07/537,664 (European Patent Application No. 90306429.3) in order to enhance the amount of the bifidobacteria-proliferating substance transferred to the permeate up to an economically paying basis, permeate flux greatly decreases. Namely, there is a case where when such a concentration factor as paying economically is tried to be attained, it takes a very long time for the treatment.

In this connection, the above U.S. patent application Ser. No. 07/537,664 (European Patent Application No. 90306429.3) has no position of prior art in judgment of the unobviousness (inventive step) of the invention of this application.

SUMMARY OF THE INVENTION

An object of this invention lies in providing a method for the purification of a bifidobacteria-proliferating substance from soybean whey according to steps free of the problems of the inventions of the above Japanese Published Patent Application Nos. 179,064/1984 and 66,978/1985 and different from the steps of them.

Another object of this invention lies in providing a method for the purification from soybean whey of a bifidobacteria-proliferating substance which is substantially free of proteins, has no bitterness and has sweetness close to sucrose and an aqueous solution of which is transparent and substantially colorless.

A still further object of this invention lies in providing an improved method for purification to enhance the occasionally lowered permeate flux in the ultrafiltration step of the invention of U.S. patent application Ser. No. 07/537,664 (European Patent Application No.

90306429.3/1990) which can afford a bifidobacteria-proliferating substance which is substantially free of proteins, has no bitterness and has sweetness close to sugar and an aqueous solution of which is transparent and substantially colorless.

The above objects of this invention were accomplished by (1) A method for the purification of a bifidobacteria-proliferating substance which comprises adjusting the temperature of soybean whey to 50° to 100° C. and the pH thereof to 6.5 to 10 either by adding an alkaline substance to the whey and heating it or by heating the whey and adding the alkaline substance, removing the formed precipitate, and ultrafiltering the resulting liquid phase part to obtain as the permeate an aqueous solution of a bifid bacteria-proliferating substance, (2) The method of the above (1) which comprises either electrodialyzing the permeate after the ultrafiltration treatment to conduct desalting, or subjecting the permeate to active carbon or porous adsorbing resin treatment to adsorb proteins, colored matters, etc. thereon and electrodialyzing the resulting active carbon or porous adsorbing resin-treated liquid to conduct desalting, and (3) The method of the above (2) which comprises subjecting the electrodialysis-treated liquid to ion exchage resin treatment to remove salts, colored substances and nitrogen compounds which may be contained in a very small amount.

DETAILED DESCRIPTION OF THE INVENTION

Figure 1:
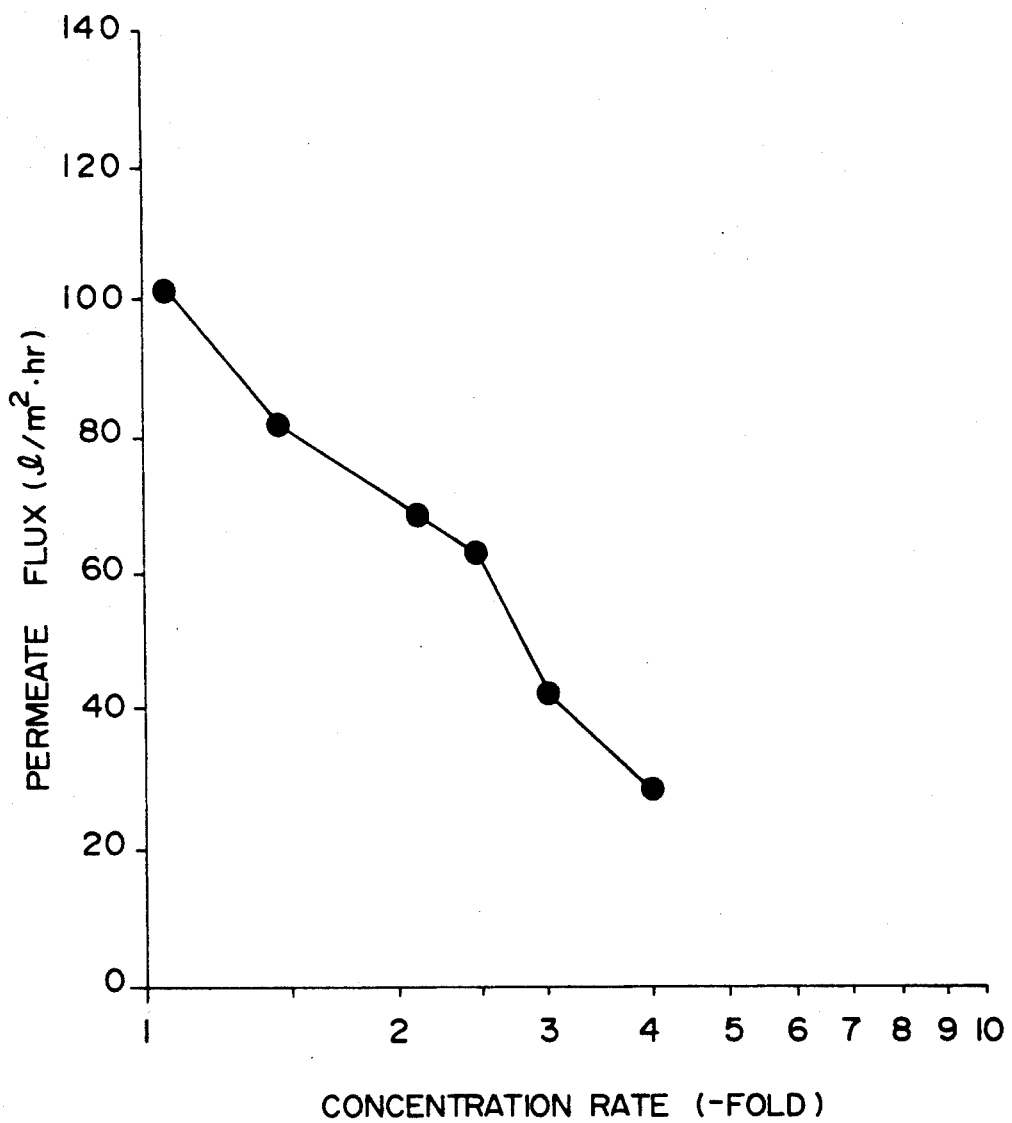
FIG. 1 shows the transition of permeate flux in the ultrafiltration step of the invention (Example 1).

Soybean whey in this invention means an aqueous solution obtained by removing the alcohol (usually together with a fair amount of water) through evaporation by vacuum concentration or the like from an extract of defatted soybeans with an aqueous alcohol solution (usually, an aqueous solution of ethanol), and is commonly referred to in the soybean processing industry as "concentrated soybean protein whey"; or an aqueous solution obtained by adding an acid (usually, phosphoric acid and/or hydrochloric acid) to an extract of defatted soybeans with water and removing the precipitated soybean proteins, or a liquid obtained by concentrating the aqueous solution by vacuum concentration or the like, and is commonly referred to in the soybean processing industry as "isolated soybean protein whey". These two kinds of soybean wheys are both industrially (and easily) obtained as a by-product after fat recovery and protein recovery from soybeans, and have not heretofore effectively been utilized.

As a previous stage before the first stage of the invention, the solid component concentration of the soybean whey is adjusted to the order of 10 to 50 in terms of R. Bx. (refractive Brix; denoting a refractive index) by, in case of the concentrated soybean protein whey, usually diluting it, or concentrating it or without any operation, or by, in case of the isolated soybean protein whey, usually concentrating it or diluting it with water, or without any operation. The is because separation efficiency in solidliquid separation after the later alkaline substance and heating treatment and efficiency in the later ultrafiltration are taken into account.

In this invention such concentrated or water-diluted soybean whey is also referred to as soybean whey.

In the first step of the invention, soybean whey is adjusted to a temperature of 50° to 100° C. and a pH of 6.5 to 10 either by adding an alkaline substance to the soybean whey and then heating the mixture or by heating the soybean whey and then adding the alkaline substance. Due to these operations, the permeate flux of the membrane in the succeeding ultrafiltration step remarkably increases.

There is no particular limitation about the alkaline substance to be used, but a hydroxide of an alkali or alkaline earth metal or a carbonate or bicarbonate of an alkali metal is usually used. Specific examples of the alkaline substance include sodium hydroxide, potassium hydroxide, calcium hydroxide, magnesium hydroxide, sodium carbonate, sodium bicarbonate, etc. Preferably the alkaline substance is used as an aqueous solution or suspension.

The pH of the soybean whey is adjusted to pH 6.5 to 10, preferably 7 to 9 with the alkaline substance. In a pH below 6.5 the formation of precipitate is insufficient and in a pH beyond 10 the resulting soyben whey is strikingly colored. The soybean whey is also heated to 50° to 100° C., preferably 60° to 80° C., and a precipitate is formed by the pH adjustment and heating. In a heating temperature below 50° C. the formation of precipitate is insufficient, and in a temperature beyond 100° C. the soybean whey is strikingly colored.

The holding time after the predetermined pH and temperature were attained by the addition of the alkaline substance and heating varies depending on operation scale, pH, temperature and the like, but preferably is on the order of 3 hours or less.

The formed precipitate is removed by centrifugation or the like and the liquid phase part is recovered. The precipitate is estimated to be phosphoric acid and phytic acid insolubilized by the alkaline substance, and colloidal proteins, colored substances, odorants and the like adsorbed thereon and precipitated.

The liquid phase part obtained after the removal of the precipitate in the previous step is then ultrafiltered to obtain as the permeate an aqueous solution of a bifid bacteria-proliferating substance. The ultrafiltration is carried out for the removal of high molecular substances, mainly proteins. When proteins remain in the final product, its flavour is sometimes undesirably influenced thereby and there is a possibility that browning reaction with saccharides takes place with heating.

The ultrafiltration is carried out using a membrane having a fractional molecular weight of 20,000 to 100,000, preferably 40,000 to 60,000 and the filtrate is collected. At a fractional molecular weight below 20,000 permeate flux becomes low and the yield of the desired substance is low, and such a fractional molecular weight is not suitable for efficient production. Further, when it goes beyonds 100,000 impurities other than the desired substance increase, and purification in the succeeding steps becomes difficult and efficient operation becomes impossible, and thus such high fractional molecular weight is not desired.

Other operation conditions in the ultrafiltration treatment are not limited by the essential contents and characteristic of the invention but limited solely by general conditions such as the durability of the membrane and economical efficiency. For example, when the concentration of the solid components in the solution to be subjected to ultrafiltration is too low, the apparatus is enlarged and economical efficiency is lowered, and when it is too high, permeate flux is largely lowered. Thus the concentration is suitably on the order of 10 to 40 in terms of R. Bx. Further, although when pressure in the ultrafiltration is raised, permeate flux increases, too high pressure makes it easy that the compaction and fouling of the membrane take place and lowers the rejection of high molecular substances. On the other hand, when the pressure is too low, sufficient permeate flux is not obtained. Therefore, proper pressure is on the order of 1 to 20 $kg/cm^2$. Although in general the higher temperature in the ultrafiltration is, the better operability is and its effect is more expected, too high temperature sometimes denatures the membrane material and in too low temperature there is a concern that microorganism contamination takes place. Therefore, the temperature is generally on the order of room temperature to 100° C., preferably on the order of 40° to 90° C. The terminus of ultrafiltration is usually expressed by a concentration rate indicating the degree of concentration of the liquid to be treated. When the concentration rate is too low, the amount of the bifidobacteria-proliferating substance to permeate and be transferred into the permeate decreases and its yield is reduced. When the concentration rate is too high, operating costs become large and it takes too much time and thus economic efficiency is lowered. Therefore, a proper concentration rate is determined taking these matters into account.

The ultrafiltration in the method of the invention is not limited in the shape and material of the membrane used therefor, and as for the shape, any of tabular, tubular, spiral and hollow fiber shapes can be adopted. Further, there is no particular limitation on the material, and there can generally be used any of cellulose acetate, polyamide, polyimide, ployacrylonitrile, polyolefin, polysulfone and inorganic materials.

The permeate after the ultrafiltration can be used as such, or as syrup after concentration by vacuum concentration or the like or as power after successive drying by freeze drying, spray drying, continuous vacuum drying or the like for the proliferation of intestinal bifidobacteria. However, the permeate contains low molecular proteins, colored substances, salts, etc. not removed by the above operations, and its application is limited in view of heat stability, color, taste, etc. Therefore, it is preferred either that the ultrafiltration permeate is then electrodialyzed for desalting, or that the ultrafiltration permeate is treated with an active carbon or porous adsorbing resin to adsorb impurities such as proteins and colored substances thereon and then electrodialyzing the active carbon or porous adsorbing resin-treated liquid for desalting.

The active carbon or porous adsorbing resin to be used in the invention is an active carbon or porous adsorbing resin capable of removing included proteins (particularly 2 S proteins), colored substances, etc. without adsorbing the bifidobacteria-proliferating substance. Examples of such an active carbon and porous adsorbing resin include active carbons and porous adsorbing resins on the market used in the food industry including the sugar industry and the like for the removal of colloidal substances (colloidal proteins, etc.), colored substances, etc. Such an active carbon is any of powdery active carbon and granular active carbon and such a porous adsorbing resin may either have ion exchange groups or not. Example of the adsorbing resin include porous strongly basic anion exchange resins, porous amphoteric ion exchange resins, etc.

The treatment with the active carbon may be carried out by any of a batch method and a column method, and the treatment with the adsorbing resin is usually carried out by a column method. In case of the treatment with the active carbon using a batch method, the amount of the active carbon to be used is an amount enough to attain the above object, and generally on the order of 0.5 to 5 wt % based on the ultrafiltration permeate.

The temperature of treatment with the active carbon or porous adsorbing resin is generally on the order of room temperature to 70° C. However, a temperature equal to or more than 40° C. is preferred in view of the avoidance of microorganism contamination. In a temperature beyond about 60° C. treatment effect generally tends to be lowered. The proper pH of the treatment is generally 8 or less, but in too low pH the hydrolysis of saccharides takes place. In case of the batch method, the time of treatment with the active carbon or porous adsorbing resin varies depending on stirring speed, temperature, etc. and cannot be described definitely, but usually the time is specifically determined by an aimed decolorization degree. In case of the column method, conditions such as flow velocity are determined so that an appropriate decolorization degree can be attained. In case of the batch method, the active carbon is separated by filtration, centrifugation or the like after the active carbon treatment.

A fairly large part of the included proteins, particularly low molecular proteins such as 2 S proteins and most of the colored substances, etc., which become a cause of membrane fouling in the succeeding electrodialysis treatment, are removed by this active carbon or porous adsorbing resin treatment.

The electrodialysis in the ivention can be carried out either following the ultrafiltration treatment or after the active carbon or porous adsorbing resin treatment. However, preferably, the dialysis is carried out after the active carbon or porous adsorbing resin treatment in view of the avoidance of fouling of the electrodialysis membrane.

The electrodialysis is generally carried out in a combination of a cation exchange membrane with an anion exchange membrane. There is no particular limitation about the ion exchange membranes to be used, and there can suitably be used a styrene-butadiene or styrene-divinylbenzene cation exchange membrane which is generally used for desalting and wherein sulfonic acid groups are made to exist, a styrene-butadiene, styrene-divinylbenzene or styrene-vinylpyridine anion exchange membrane which is generally used for desalting and wherein quaternary ammonium groups are made to exist, etc.

Although higher temperature of electrodialysis gives better efficiency, too high temperature has a bad influence on the ion exchange membranes (deterioration of the membranes). Further in a temperature below 40° C., there is a concern of microorganism contamination. Therefore, the temperature is generally room temperature to 70° C., preferably 40° to 60° C. When the electric current value in the electrodialysis is too high, electrolysis occurs and heat is generated, whereas when it is too low, the efficiency of desalting is lowered. Thus, the current value is specifically determined in a range less than the limiting electric current density taking the apparatus, membrane area, the ionic strength and temperature of the liquid to be treated, etc. into account. When the solid component concentration of the liquid to be treated in electrodialysis is too high, too heavy loads are born on the membranes, whereas when it is too low, desalting efficiency is lowered to lack economical efficiency. Therefore, the concentration is specifically determined taking these matters into account. The terminus of electrodialysis is determined taking objects to which the product is applied, loads onto the succeeding ion exchange resin treatment, etc. into account. Namely, electrodialysis is ceased when proper electric conductivity is attained.

The electrodialysis-treated liquid can be used as such, or as syrup after concentration by vacuum concentration or the like or as powder after successive drying by feeze drying, spray drying, continuous vacuum drying or the like for the proliferation of bifidobacteria. However, the electrodialysis-treated liquid sometimes contains very small amounts of salts, colored substances, nitrogen compounds, etc., and there is a case where these very small amounts of salts and nitrogen compounds become a cause of bitterness or the colored substances spoil the color of beverages. In these cases, it is preferred that the electrodialysis-treated liquid is further subjected to ion exchange resin treatment.

This ion exchange resin treatment can usually be carried out by a combination of an cation exchange resin with an anion exchange resin, an amphoteric ion exchange resin, or a combination of them.

Ion exchange resins used for the ion exchange resin treatment are not particularly limited, and there can, for example, be used those used for the desalting, decolorization, etc. of saccharide liquids. Examples of the cation exchange resin include gel type or porous type styrene-divinylbenzene strongly acidic cation exchange resins, and (meth)acrylic acid-divinylbenzene weakly acidic cation exchange resins, and examples of the anion exchange resin include gel type or porous type styrene-divinylbenzene strongly basic anion exchange resins, and acrylic acid-divinylbenzene weakly basic anion exchange resins and sytrene-divinylbenzene weakly basic anion exchange resins.

Although the ion exchange resin treatment can be carried either by a batch method or by a column method, the column method is preferred. When the temperature of the ion exchange resin treatment is high, the hydrolysis of saccharides takes place, and in a temperature around room temperature microorganism contamination becomes a problem. Therefore, a temperature of 0° to 10° C. is, for example, suitable.

The ion exchange resin-treated liquid is concentrated by vacuum concentration or the like, and dried into powder by freeze drying, spray drying, continuous vacuum drying or the like to obtain a bifidobacteria-proliferating substance. The bifidobacteria-proliferating substance obtained in the invention has refreshing sweetness very close to sucrose and smooth taste and further has stability againt acids and heat equal to sucrose. Thus, it can be utilized as a substitute of sucrose in various foods including beverages, desserts and confectionery. The bifidobacteria-proliferating substance obtained by the present purification method can be used not only as powder but, for example as the ion exchange resin-treated liquid or syrup obtained by vacuum concentrating it. When the bifidobacteria-proliferating substance obtained by the invention is drunk or eaten as such or in a form applied to food, the proliferation of intestinal bifidobacteria can be promoted.

The invention is further specifically described according to examples.

EXAMPLE 1

700 L of an aqueous 60 v/v % ethyl alcohol solution was added to 100 kg of defatted soybean powder (produced by THE NISSHIN OIL MILLS, LTD,) and the mixture was stirred with heating at 60° C. for 30 minutes. After the heating and stirring, the insoluble matters were removed by filtration, and ethyl alcohol was removed from the filtrate by vacuum distillation to obtain 130 kg of concentrated soybean protein whey (pH 5.8) (solid component concentration R. Bx. of 63.2).

38 kg of water was added to 18 kg of the thus obtained concentration soybean protein whey, the mixture was heated up to a temperature of 70° C., and 0.4 kg of a 25 wt % aqueous calcium hydroxide suspension was added to adjust the pH to 7.8.

The mixture was centrifuged using a centrifuge (SA-1 type) produced by Far East Westfalia Separator Co., Ltd. The adopted centrifugation conditions were a revolution number of 9,000 rpm, a mixture feed speed of 50 L/hr and a desludge frequency of 26 times/hr.

39 kg of the obtained supernatant was ultrafiltered using a ceramic ultrafilter (produced by Nippon Gaishi Co., Ltd.). The ultrafiltration conditions were a circulating liquid temperature of 70° C., a linear velocity of 5 m/sec, a pressure of 3 kg/cm$^2$, a fractional molecular weight of the ceramic membrane of 50,000 and a membrane area of 0.24 m$^2$. The transition of permeate flux before a fourfold concentration, namely about 29 kg of the permeate was obtained was good as shown in FIG. 1. Thus, as the permeate was obtained a clear liquid free of proteins having a molecular weight of 50,000 or more and containing stachyose and raffinose.

EXAMPLE 2

A bifidobacteria-proliferating substance was obtained according to the same procedure as in Example 1 except that 0.97 kg of a 10 wt % aqueous sodium hydroxide solution was used as an alkaline substance in place of the 25 wt % aqueous calcium hydroxide suspension in Example 1. Likewise in Example 1, proteins having a molecular weight of 50,000 or more were removed and a clear liquid was obtained containing stachyose and raffinose.

EXAMPLE 3

Powdery active carbon (FC-W50 produced by Futamura Chemical Industry Co., Ltd.) was added by 2% to the permeate obtained after the ultrafiltration treatment in Example 1, and they were mutually contacted at 30° to 50° C. for about 1 hour. Then, filtration was carried out using a filter press filter.

Then, electrodialysis was carried out using a electrodialysis apparatus (TS-2 type produced by Tokuyama Soda Co., Ltd.). In the electrodialysis was used an ion exchange membrane consisting of 10 pairs of 2 dm$^2$ each of anionic membranes and cationic membranes. Desalting was carried out under operation conditions of an initial voltage of 4 V, an initial current of 9.4 A, a final voltage of 9.4 V, a final current of 1.56 A and a liquid temperature of 30° to 50° C. until the electric conductivity of the liquid reached 3 mS/cm.

The electrodialyzed liquid was cooled to 10° C. or less followed by ion exchange treatment. The liquid was passed through a cation exchange column (Diaion PK216, 2.7 L), an anion exchange column (Diaion WA30, 2.7 L) and a mixed column (Diaion PK216, 0.3 L; Diaion PA408, 0.6 L) in this order to obtain an ion exchanged liquid. 39 kg of the ion oxchanged liquid was obtained.

Various data of the treated liquid after each of the above steps are shown in Table 1.

TABLE 1

| Step sample | R.Bx. | Electric conductivity (mS/cm) | Coloring degree (OD$_{500}$) | Crude protein (%) |
| --- | --- | --- | --- | --- |
| UF permeate | 17.1 | 14.28 | 0.89 | 0.83 |
| Active carbon-treated liquid | 16.2 | 12.41 | 0.21 | 0.73 |
| Electrodialysis-treated liquid | 14.5 | 2.52 | 0.12 | 0.59 |
| Ion exchange resin-treated liquid | 9 | 0 | 0 | 0.01 |

UF: ultrafiltration

EXAMPLE 4

A bifidobacteria-proliferating substance was obtained according to the same manmer as in Example 3 except that 0.97 kg of a 10 wt % aqueous sodium hydroxide solution was used an alkaline substance in place of the 25 wt % aqueous calcium hydroxide suspension. The resulting ion exchanged bifidobacteria-proliferating substance-containing liquid was a similar product to that of Example 3.

EXAMPLES 5 AND 6 AND COMPARATIVE EXAMPLE 1

324.3 g of water was added to 175.7 g of concentrated soybean protein when having R. Bx. of 56.9 (produced by The Nissin Oil Mills Ltd.), and the mixture was heated up to 70° C. to prepare a sample having R. Bx. of 20 and a pH of 5.8. On the other hand, a 25 wt % aqueous calcium hydroxide suspension was added to the same concentrated soybean protein whey as above diluted in the same manner as above to simultaneously prepare samples having pH values of 7.8 and 8.8 and R. Bx. of 20, respectively.

These liquids were each centrifuged using a centrifuge (produced by Hitachi, Ltd., Model 20RP-52). Centrifugation conditions were a revolution number of 5,000 rpm (3,000 G) and a time of 5 minutes, and 500 g each of the fed liquids was treated. The centrifuged liquids were composed of the supernatant of 85.1 to 87.2% and the sediment of 12.8 to 14.9%. 300 g each of 425.5 to 436 g of the resulting supernatants was ultrafiltered using a circulation type flat membrane testing machine (Model P-28, produced by DAICEL CHEMICAL INDUSTRIES, LTD.,). The treating conditions were a circulating liquid temperature of 70° C., a linear velocity of 2.2 m/sec, a pressure of 10 kg/cm$^2$, a fractional molecular weight of the membrane of 40,000 and a membrane area of 0.0028 m$^2$.

Figure 2:
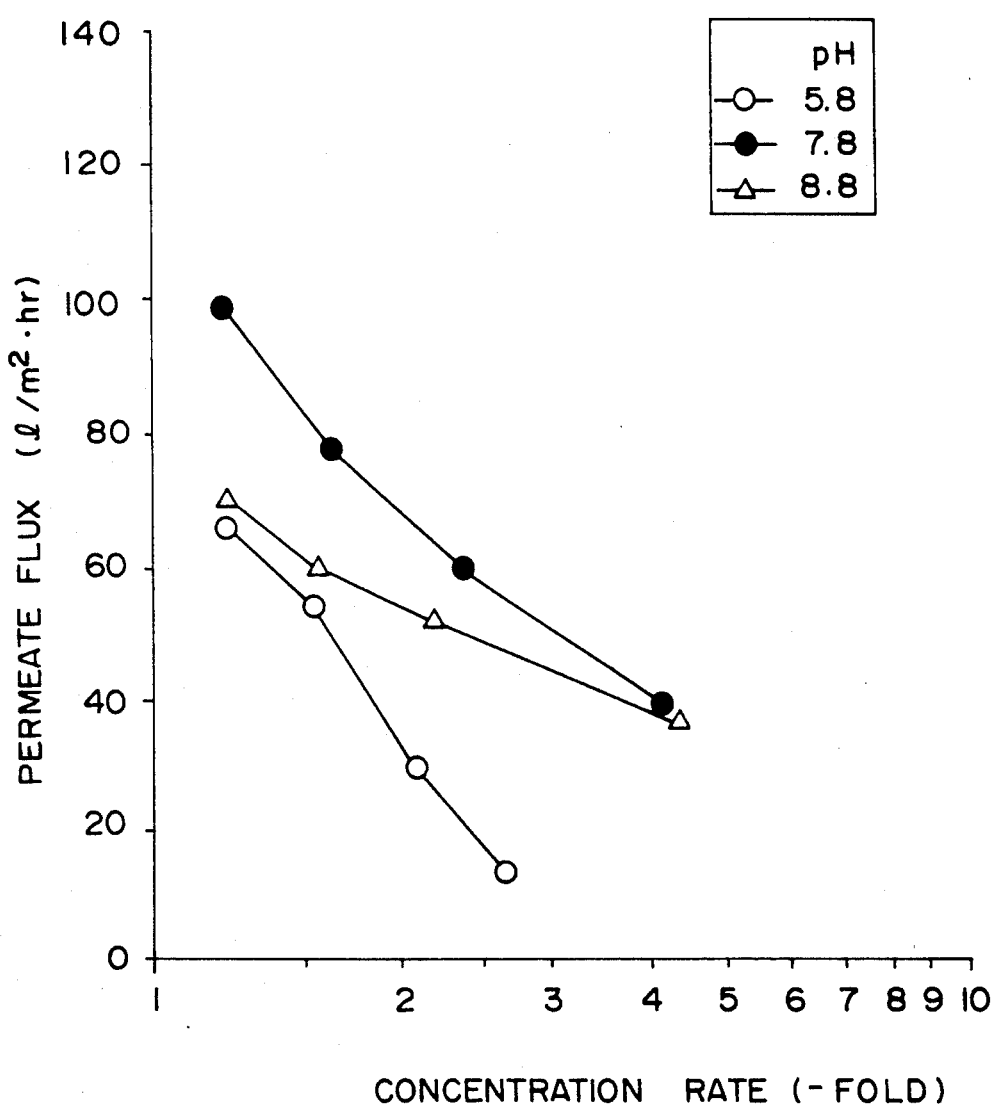
FIG. 2 shows the influence of the alkali substance and heating treatment on permeate flux in the ultrafiltration step of the invention (Soybean whey derived from an aqueous alcohol solution-extracted extract was used. Examples 5 and 6 and Comparative example 1).

In the transition of permeate flux before a fourfold concentration, namely about 225 g of the permeate was obtained, better results were obtained in pH values of the samples of 7.8 and 8.8 compared to pH 5.8, as shown in FIG. 2. Further, average permeate fluxes before the fourfold concentration was attained were 30.8 L/m$^2$·hr, 60.5 L/m$^2$·hr and 49.6 L/m$^2$·hr at pH values of 5.8, 7.8 and 8.8, respectively.

As the ultrafiltration permeate at pH 7.8 was obtained a clear liquid freed of proteins having a molecuar weight of 40,000 or more, containing stachyose and raffinose, and having R. Bx of 15.1 and an electric conductivity of 10.4 mS/cm.

EXAMPLE 7 AND COMPARATIVE EXAMPLE 2

390 g of water was added to 200 g of isolated soybean protein whey having R. Bx. of 59.9 (produced by Asahi Yushi Kogyo Co., Ltd)., the mixture was heated up to 70° C., and a 25 wt % aqueous calcium hydroxide suspension was added to ad just the pH to 5.8, whereby a sample having R. Bx. of 20 was prepared. A 25 wt % aqueous calcium hydroxide suspensionwas added to the same isolated soybean protein whey as above diluted in the same manner as above to adjust the pH to 7.8, whereby a sample having R. Bx. of 20 was simultaneously prepared.

These liquids were each centrifuged using a centrifuge (produced by Hitachi, Ltd., Model 20 RP-52). Centrifugation conditions were a revolution number of 5,000 rpm (3,000 G) and a time of 5 minutes, and 600 g each of the fed liquids was treated. 405 g and 407 g of the supernatants were obtained from the pH 5.8 sample and the pH 7.8 sample, respectively. 300 g each of the supernatants was ultrafiltered using a circulation type flat membrame testing machine (Model P-28, produced by DAICEL CHEMICAL INDUSTRIES, LTD.). The treating conditions were a circulating liquid temperature of 70° C., a linear velocity of 2.2 m/sec, a pressure of 10 kg/cm$^2$, a fractional molecular weight of membrane of 40,000 and a membrane area of 0.0028 m$^2$.

Figure 3:
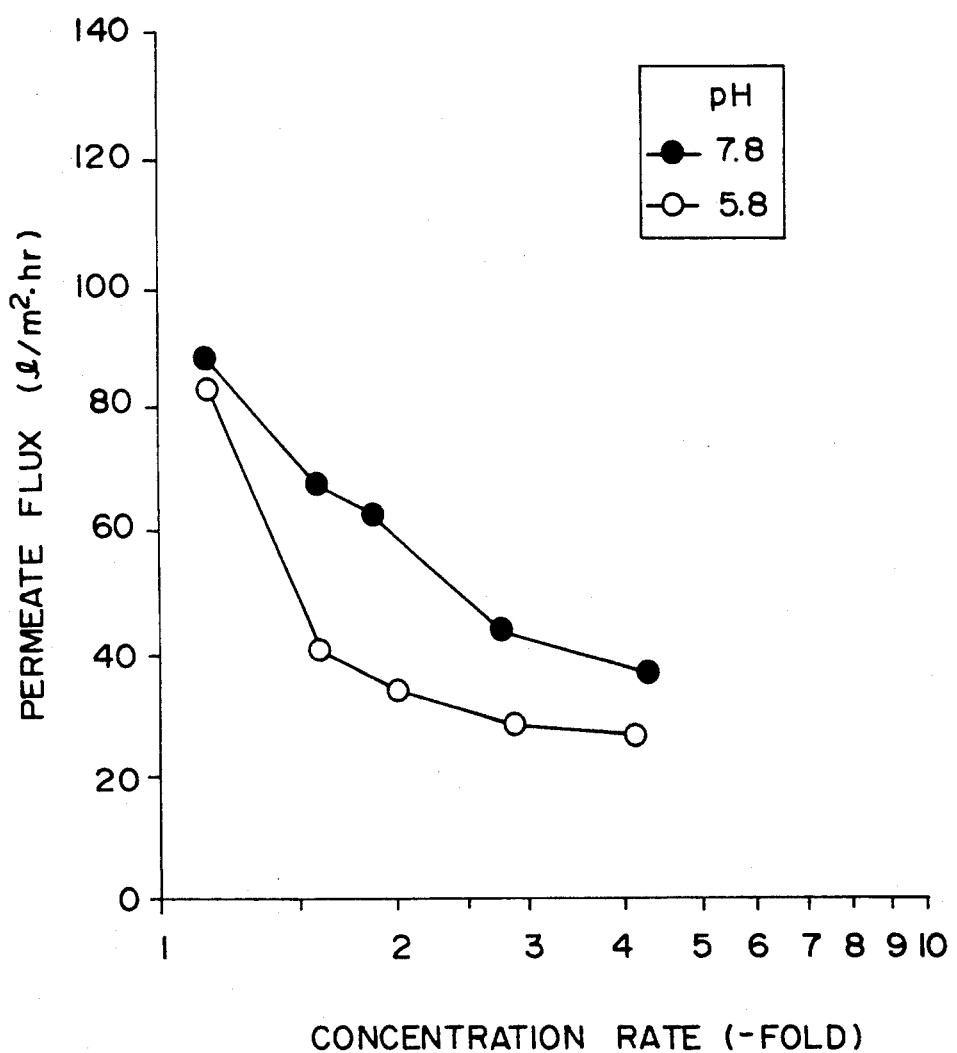
FIG. 3 shows the influence of the alkali substance and heating treatment on permeate flux in the ultrafiltration step of the invention (Soybean whey derived from a water-extracted extract was used. Example 7 and Comparative example 2).

In the transition of permeate flux before a fourfold concentration, namely about 225 g of the permeate was obtained, better results were obtained in a pH of the samples of 7.8 compared to pH 5.8, as shown in FIG. 3. Further, average permeate fluxes before the fourfold concentration was attained were 41.6 L/m$^2$·hr and 57.6 L/m$^2$·hr at pH values of 5.8 and 7.8, respectively.

As the ultrafiltration permeate at pH 7.8 was obtained a clear liquid freed of proteins having a molecular weight of 40,000 or more, containing stachyose and raffinose, and having R. Bx. of 16.7 and an electric conductivity of 27.3 mS/cm.

REFERENCE EXAMPLE 1

An ingestion test was carried out in order to ascertain the intestinal bifidobacteria proliferation effect by the ingestion of the bifidobacteria-proliferating substance, obtained in an industrial production scale by basically the same process as in Example 3. Six healthy male adult volunteers (28 to 48 years old) ingested the bifidobacteria-proliferating substance (powder powdered by continuous vacuum drying) in an amount of 10 g/day successively for 3 weeks. One week prior to the start of the test to the completion of the test, each volunteer was allowed to maintain a normal diet, but not to take pharmaceuticals and viable cell agents (including lactic acid bucteria products). Fecal samples were collected from each volunteer immediately before the ingestion test, 7 days, 14 days and 21 days (the completion time of the ingestion test period) after the ingestion test, and 14 days after the completion of the ingestion test, and the evaluation of fecal flora was made. The evaluation of fecal flora was made according to the method of Mitsuoka [T. Mitsuoka, "Chonaikin no Sekai—Kenkiseikin no Bunri to Dotei" (The World of Intestinal Bacteria Flora—the Separation and Identification of Anaerobes), 319, 45(1982), Published by Sobunsha, Tokyo]. The test results are shown in

TABLE 2

|  | Fecal bifidobacteria number* |
|---|---|
| Immediately before the ingestion | 9.5 ± 0.5 (A) |
| Average value during the ingestion | 10.0 ± 0.4 (B) |
| After the ingestion | 9.3 ± 0.5 (C) |

*Logarithmic average value ± standard deviation of bifidobacteria number in 1 g of the feces
Significant difference of B to A (t-test) $p < 0.01$
Significant difference of B to C (t-test) $p < 0.001$

What is claimed is:

1. A method of preparing an aqueous soy extract substantially free of proteins having a molecular weight 100,000 or greater, the aqueous soy extract enhancing the proliferation of bifidobacteria, said method comprising the steps of:
   (1) to a soybean whey selected from concentrated soybean protein whey substantially precluding discoloration by or isolated soybean protein whey, adjusting the pH to 6.5 to 10 and adjusting the temperature to 50° C. to 100° C. by only, either
      (a) adding an alkaline substance to the whey then heating it, or
      (b) heating the whey and adding an alkaline substance to it to form a precipitate;
   (2) removing the precipitate formed in step (1) and recovering the resulting liquid phase; and thereafter
   (3) ultrafiltering the liquid phase of step (2) to remove substantially all of the proteins having a molecular weight of 100,000 or more to produce an aqueous solution that enhances the proliferation of bifidobacteria.

2. The method of claim 1 wherein the soybean whey is an aqueous solution obtained by removing the alcohol through evaporation from an extract of defatted soybean with an aqueous alcohol solution and if necessary diluting or concentrating the resulting solution, or an aqueous solution obtained by adding an acid to an extract of defatted soybean with water, removing the precipitated soybean proteins and if necessary successively concentrating the resulting solution.

3. The method of claim 1 wherein the alkaline substance is an alkali metal on alkaline earth metal hydroxide, or an alkali metal carbonate or bicarbonate.

4. The method of claim 1 wherein the ultrafiltration is carried out using an ultrafiltration membrane having a fractional molecular weight of 20,000 to 100,000.

5. The method of claim 1 which comprises either electrodialyzing the permeate after the ultrafiltration treatment to conduct desalting, or subjecting the permeate to active carbon or porous adsorbing resin treatment to adsorb proteins, colored substances, etc. thereon and electrodialyzing the resulting active carbon or porous adsorbing resin-treated liquid to conduct desalting.

6. The method of claim 5 which comprises subjecting the electrodialysis-treated liquid to ion exchange resin treatment to remove salts, colored substances and nitrogen compounds which may be contained in a very small amount.

* * * * *